United States Patent
Lellouche et al.

(10) Patent No.: US 10,576,224 B2
(45) Date of Patent: Mar. 3, 2020

(54) METHOD FOR DETECTING AT LEAST ONE ANOMALY IN AN OBSERVED SIGNAL, CORRESPONDING COMPUTER PROGRAM PRODUCT AND DEVICE

(71) Applicants: Univesite De Bretagne Occidentale, Brest (FR); Institut Mines-Telecom, Brest (FR)

(72) Inventors: Francois Lellouche, Quebec (CA); Erwan L'Her, Brest (FR); Dominique Pastor, Plouzane (FR); Quang-Thang Ngyuen, Brest (FR)

(73) Assignees: UNIVERSITE DE BRETAGNE OCCIDENTALE, Brest (FR); INSTITUT MINES-TELECOM, Brest (FR)

( * ) Notice: Subject to any disclaimer, the term of this patent is extended or adjusted under 35 U.S.C. 154(b) by 1359 days.

(21) Appl. No.: 14/387,507

(22) PCT Filed: Mar. 22, 2013

(86) PCT No.: PCT/EP2013/056138
§ 371 (c)(1),
(2) Date: Sep. 23, 2014

(87) PCT Pub. No.: WO2013/139979
PCT Pub. Date: Sep. 26, 2013

(65) Prior Publication Data
US 2015/0034083 A1     Feb. 5, 2015

(30) Foreign Application Priority Data
Mar. 23, 2012 (FR) ..................... 12 52660

(51) Int. Cl.
*A61M 16/00* (2006.01)

(52) U.S. Cl.
CPC .... *A61M 16/0051* (2013.01); *A61M 16/0057* (2013.01); *A61M 2205/3303* (2013.01);
(Continued)

(58) Field of Classification Search
CPC ........... G06K 9/00496; G06K 9/00536; A61M 16/0051; A61M 16/021; A61M 16/0057;
(Continued)

(56) References Cited

U.S. PATENT DOCUMENTS

| | | |
|---|---|---|
| 2005/0232096 A1 | 10/2005 | Van Helvoirt et al. |
| 2010/0147305 A1 | 6/2010 | Dellaca' et al. |
| 2010/0275921 A1* | 11/2010 | Schindhelm ............. A61B 5/08 128/204.23 |

FOREIGN PATENT DOCUMENTS

EP    2281506 B1    1/2013

OTHER PUBLICATIONS

Lamotte et al., Detection and Characterization of Dynamic Jump in Differed Time: Application to the Segmentation of the EMG, Fifteenth GRETSI Symposium on Signal Image Processing, pp. 1-17—translation (Year: 1995) (Year: 1995).*

(Continued)

*Primary Examiner* — Sujoy K Kundu
*Assistant Examiner* — L. Anderson
(74) *Attorney, Agent, or Firm* — David D. Brush; Westman, Champlin & Koehler, P.A.

(57) ABSTRACT

A method is provided for detecting the presence of an anomaly within an observed physical signal. The observed signal includes an addition of a physical disturbance signal and a reference signal. The anomaly is relative to a change in the behavior of the reference signal compared with a first tolerance value. Such a method includes: determining a time span having at least one moment of interest; detecting the presence of the anomaly within the observed physical signal (Continued)

Figure 1:
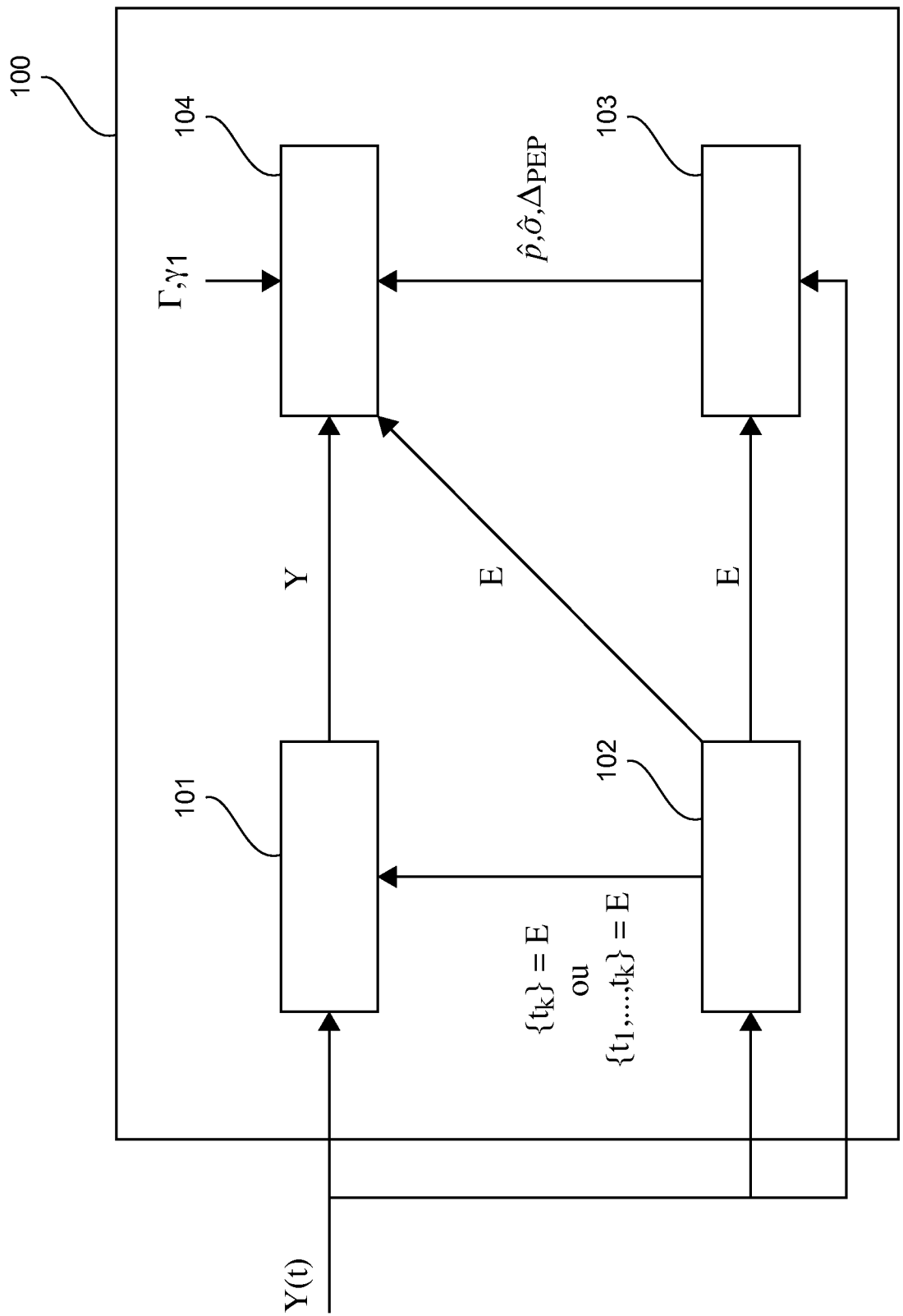

during the time span by conducting a hypothesis test using the first tolerance value, a first rate of tolerated false alarms, and data obtained from processing the observed signal.

15 Claims, 7 Drawing Sheets

(52) U.S. Cl.
CPC ..... *A61M 2205/50* (2013.01); *A61M 2230/04* (2013.01); *A61M 2230/10* (2013.01); *A61M 2230/205* (2013.01); *A61M 2230/30* (2013.01); *A61M 2230/40* (2013.01)

(58) Field of Classification Search
CPC ........ A61M 2230/30; A61M 2230/205; A61M 2230/40; A61M 2230/10; A61M 2230/04; A61M 2230/06; A61M 2230/08
See application file for complete search history.

(56) References Cited

OTHER PUBLICATIONS

Maarsingh et al ., Respiratory muscle activity measured with a noninvasive EMG technique technical aspects and reproducibiliyt, 2000, J Appl Physiol, pp. 1955-1961 (Year: 2000).*

International Search Report and Written Opinion dated Apr. 4, 2013 for corresponding International Application No. PCT/EP2013/056138, filed Mar. 22, 2013.

Lamotte, "Detection et Characterisation en temps differe de sauts de dynamique: application a le segmentation de 1 EMG", Jan. 1, 1995 (Jan. 1, 1995), Jan. 1, 1995, pp. 1189-1192, XP055055952.

International Preliminary Report on Patentability and English translation of the Written Opinion dated Sep. 23, 2014 for corresponding International Application No. PCT/EP2013/056138, filed Mar. 22, 2013.

French Search Report and Written Opinion dated Mar. 11, 2013 for corresponding French Application No. 1252660, filed Mar. 23, 2012.

R.J. Riella et al., "Method for automatic detection of wheezing in lung sounds", Brazilian Journal of Medical and Biological Research (2009) 42: 674-684.

Wulsin et al., "Semi-Supervised Anomaly Detection for EEG Waveforms Using Deep Belief Nets", Ninth International Conference on Machine Learning and Applications (ICMLA), 2010.

Y. Zhu, "Automatic Detection of Anomalies in Blood Glucose Using a Machine Learning Approach", in IEEE International Conference on Information Reuse and Integration (IRI), 2010.

English translation of Lamotte, "Bath Mode Dynamic Jump Detection and Characterization: Application to EMG Segmentation", Jan. 1, 1995 (Jan. 1, 1995), Jan. 1, 1995, pp. 1189-1192, XP055055952.

* cited by examiner (a)

(b)

(a)

(b)

METHOD FOR DETECTING AT LEAST ONE ANOMALY IN AN OBSERVED SIGNAL, CORRESPONDING COMPUTER PROGRAM PRODUCT AND DEVICE

1. CROSS-REFERENCE TO RELATED APPLICATIONS

This application is a Section 371 National Stage Application of International Application No. PCT/EP2013/056138, filed Mar. 22, 2013, the content of which is incorporated herein by reference in its entirety, and published as WO 2013/139979 on Sep. 26, 2013, not in English.

2. FIELD OF THE INVENTION

The field of the invention is that of the processing of a signal observed via a measurement sensor.

More specifically, the invention relates to a technique for detecting at least one anomaly present in the observed signal and related to the occurrence of an unpredictable physical phenomenon.

The invention has many applications such as for example in the field of medicine and it can be implemented in devices for monitoring the progress of a patient's physiological parameters.

More generally, it can be applied in all cases where the detection of an anomaly of a signal representing the progress of physical parameters is important for corrective operations to be performed subsequently.

3. TECHNOLOGICAL BACKGROUND

We shall strive more particularly here below in the document to describe the set of problems and issues that the inventors of the present patent application have confronted in the field of the monitoring of the respiratory flow of a patient on artificial respiration. It may be recalled that the respiratory flow corresponds to the volume of air flowing in the lungs per unit of time. The invention is naturally not limited to this particular field of application but is of interest for any technique of monitoring that has to cope with similar or proximate problems. Indeed, the present technique can be used to detect anomalies (also called irregularities or deviations) in relation to the "normal" (i.e. anomaly-free) behavior of any one of the following signals:

- electrocardiogram (ECG) signals which are signals representing the progress of the electrical potential that commands the muscular activity of a patient's heart, as a function of time, measured by electrodes placed on the surface of the patient's skin;
- electroencephalogram (EEG) signals which are signals representing the progress of the electrical activity of the brain, as a function of time, measured by electrodes placed on a patient's scalp;
- signals representing the progress of arterial pressure as a function of time;
- signals representing the progress of the oxygen concentration in tissues as a function of time;
- signals representing the progress of intracranial pressure.

This list is naturally not exhaustive and the present invention cannot be limited only to these fields of application. Indeed, it can be applied to any signal representing the progress of a patient's physiological parameters.

In the field of medical monitoring and artificial respiration, one vital parameter for which special monitoring has to be performed is that of monitoring of curves of the flow and pressure in the air passages. Indeed, in the case of incomplete or limited expiration, especially among patients with chronic obstructive pulmonary disease or with asthma, a phenomenon of air capture can arise causing thoracic distension. Thus, the lung pressure (Auto-PEEP or intrinsic positive and expiratory pressure) at the end of the expiration increases when such a phenomenon occurs. The presence of thoracic distension also results in the respiratory flow not returning to zero before the next inspiration begins.

This phenomenon of thoracic distension occurs in about 40% of patients under artificial respiration (or mechanical respiration) and it can have many harmful, physical consequences. Depending of the level of resistance and compliance of the patient's respiratory system, and therefore his time constant, clinically significant thoracic distension can occur gradually within a period of a few minutes.

It may be recalled that the goal of artificial respiration (or mechanical respiration) is to assist or replace a patient's spontaneous respiration if this respiration becomes inefficient or, in certain cases, totally absent. Artificial respiration is practiced mainly in the case of critical care (emergency medicine, intensive or intermediate care), but is also used in home care among patients having chronic respiratory deficiency.

This means that the detection of thoracic distension (i.e. the detection of Auto-PEEP) is important to enable the practitioner (or clinician) to take the action needed to reduce this phenomenon (for example by modifying the ventilator settings and extending the expiratory time).

PEEPi can only be quantified at specific points in time through the performance of an expiratory pause enabling measurement of the expiratory equilibrium pressure.

Figure 2A:
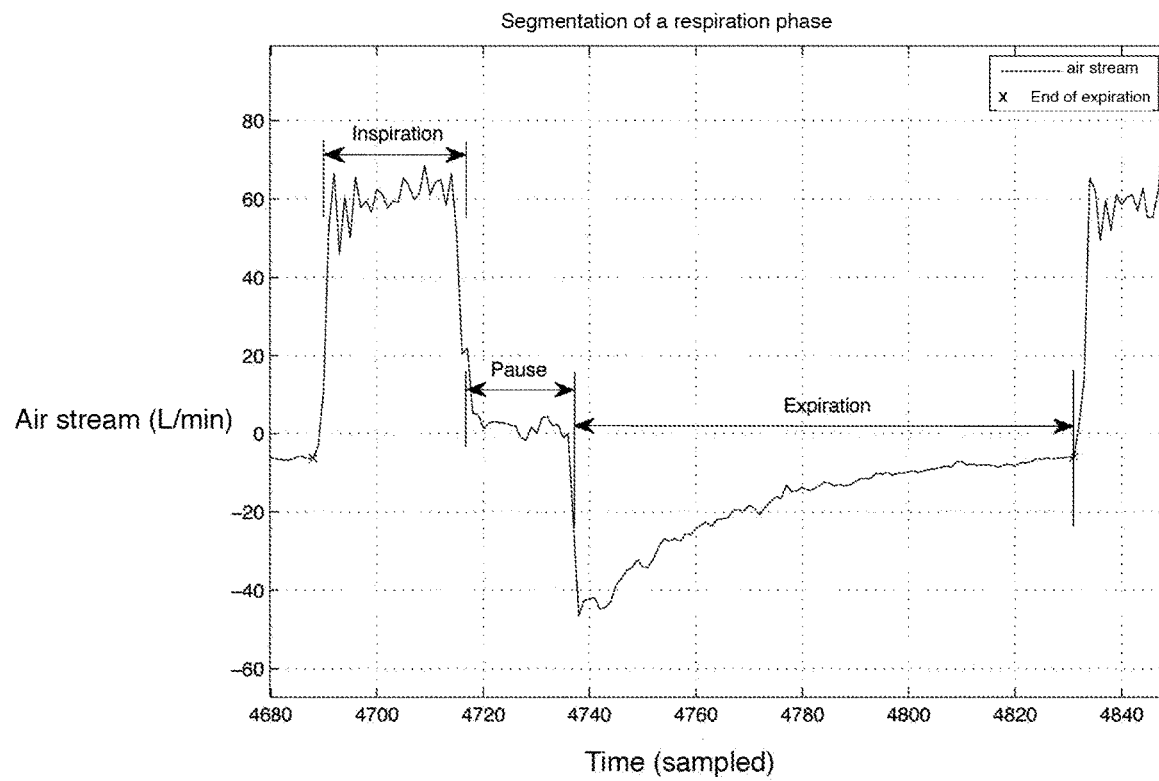
Figure 2B:
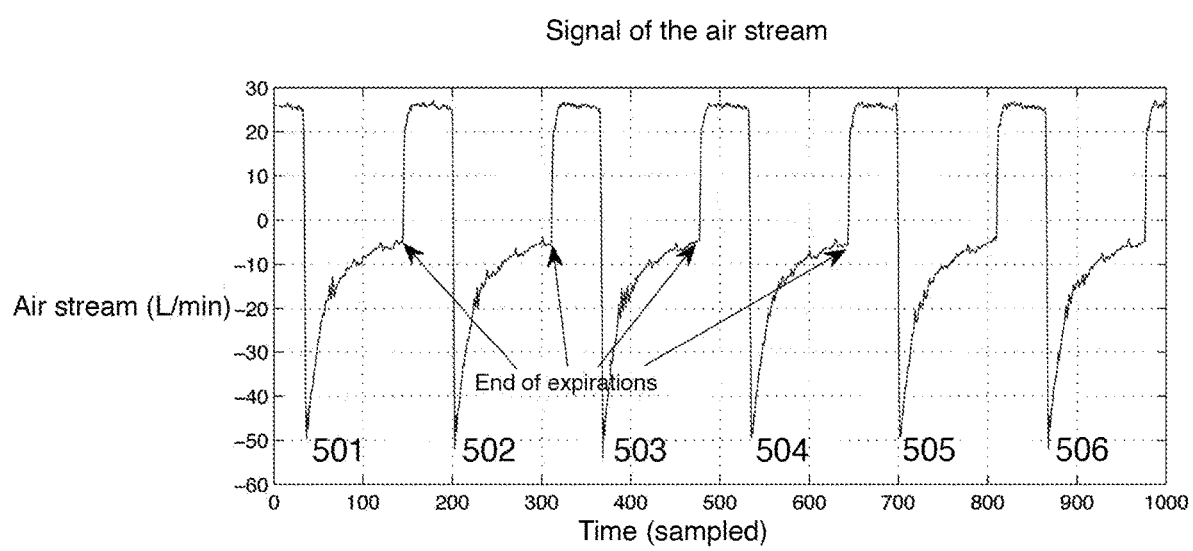

The progress of intra-pulmonary pressure can however be deduced from an analysis of the signal representing the progress of the air flow (in L/min) (i.e. the progress of the volume of the air inspired and expired by the patient as a function of time, also called the respiratory flow curve) of a patient measured through sensors positioned for example at the ventilator. This means that a thoracic distension (i.e. an Auto-Peep) can be detected through the study of such a signal. FIGS. 2(a) and 2(b) respectively present the characteristic phases (or segments) of such a signal during a respiration cycle comprising an inspiration, a pause and an expiration and a signal representing the progress of a patient's respiratory flow as a function of time, which includes a plurality of respiratory cycles.

There is a first technique known in the prior art, described in the US document US2010147305, called "System and Method for the Automatic Detection of the Expiratory Flow Limitation", which can be used, through automated processing, to detect a limitation of flow in the patient.

However, this technique has various drawbacks, especially that of requiring the integration of numerous sensors (entailing a large amount of dead space) as well as the use of regular variations of ventilator parameters to enable this measurement. While this system can be envisaged in spontaneous ventilation and during an exploration of respiratory function, its use in an artificial ventilation circuit seems to be more complicated. Besides, this technique does not seem to be capable of enabling continuous and sequential analysis of the occurrence of the phenomenon of distension and is not suited to the detection of a thoracic distension related to a problem of interface between the patient and the ventilator.

There is also another technique known in the prior art, applied to the detection of anomalies in curves presenting the progress of the glucose level present in a patient's blood, described in the document by Y. Zhu, "*Automatic Detection* of Anomalies in Blood Glucose Using a Machine Learning Approach", in *IEEE International Conference on Information Reuse and Integration (IRI)*, 2010, which those skilled in the art could apply to the present case.

In addition, there is another technique also known in the prior art, applied to the detection of anomalies in encephalograms described in the document by Wulsin et al., "*Semi-Supervised Anomaly Detection for EEG Waveforms Using Deep Belief Nets*", Ninth International Conference on Machine Learning and Applications (ICMLA), 2010, which those skilled in the art could apply to the present case.

Finally, there is also another technique known in the prior art applied to the detection of anomalies described in the document by R. J. Riella et al., "*Method for automatic detection of wheezing in lung sounds*", Brazilian Journal of Medical and Biological Research (2009) 42: 674-684, which those skilled in the art could apply to the present case.

One major drawback of these techniques lies in the fact that they require the implementation of a learning phase using a first data base followed by a validation phase using a second data base that is independent of the first data base.

4. SUMMARY OF THE INVENTION

One particular embodiment of the invention proposes a method for detecting the presence of an anomaly $\Delta(t)$ included in an observed physical signal $Y(t)$, said observed signal comprising an addition of a physical disturbance signal $X(t)$, and a reference signal $f(t)$, and said anomaly being relative to a modification of the behavior of the reference signal $f(t)$ relative to a first tolerance value $(\tau,\tau_0)$. Such a method is characterized in that it comprises:
  a step for determining a temporal set E comprising at least one instant of interest $(t_k; \{t_1, \ldots, t_K\})$;
  a step for detecting the presence of said anomaly within said observed physical signal in said temporal set E by carrying out a hypothesis test using said first tolerance value $(\tau,\tau_0)$, a first rate of tolerated false alarms $(\gamma_1)$, and data $(p,Y)$ obtained from a processing of the observed signal $Y(t)$.

Thus, the general principle of the invention is that of carrying out a hypothesis test in order to detect such an anomaly.

Such a method makes it possible to achieve the above-mentioned goals. Thus, the use of such a method makes it possible to detect anomalies in real time, and this is crucial in medical applications.

In addition, such an observed physical signal $Y(t)$ represents the progress of a patient's physiological parameters.

According to one particular aspect of the invention, such a method for detecting is characterized in that the step for determining comprises:
  a step for applying a wavelet transform to the observed signal during a time of observation, said step for applying delivering coefficients;
  a step for comparing absolute values of said coefficients with a first threshold where a function $\lambda_{\gamma_2}(\rho)$ is the unique solution in $\eta$ of an equation $1-[\Phi(\eta-\rho)-\Phi(-\eta-\rho)]=\gamma_2$, where a function $\Phi(\bullet)$ is the distribution function of a standard normal random variable, $\gamma_2$ is a second rate of tolerated false alarms, $\sigma_X$ is the deviation of the noise $X(t)$, L is a size of the sample of said observed signal and a is a value close to $\sqrt{2\ln L}$, said step for comparing delivering at least one instant of interest when the absolute value of one of said coefficients is above said threshold $\lambda_{SNT}$.

According to one particular aspect of the invention, such a method for detecting is characterized in that the step for determining comprises a filtering step.

According to one particular aspect of the invention, such a method for detecting is characterized in that it also comprises a step for smoothing the observed signal.

According to one particular aspect of the invention, such a method for detecting is characterized in that said step for detecting comprises:
  a step for projecting the observed physical signal along a vector of form p of the reference signal, said step for projecting delivering a projected value u for said at least one instant of interest $(t_k)$; and
  a step for comparing an absolute value of said projected value u and a second threshold $\lambda_{\gamma_1}^*=Q_{|\tau+w|}(1-\gamma_1)$ where $\gamma_1$ is said rate of tolerated false alarms, $\tau$ is said first tolerance value, Q is a quantile function of a random variable $|\tau+w|$ where w is a projection of said physical disturbance signal, along said vector of form p, said step for comparing corresponding to said hypothesis test and enabling the detection of an anomaly when the absolute value of said projected value u is above said second threshold $\lambda_{\gamma_1}^*$.

Thus, in this embodiment, such a hypothesis test uses only said first tolerance value, said first rate of tolerated false alarms and said data obtained from a processing of the observed signal. This hypothesis test therefore does not necessitate the explicit knowledge of the model of the reference signal.

According to one particular aspect of the invention, such a method for detecting is characterized in that when said set E comprises K instants of interest $(t_1, \ldots t_K)$ and when the values of the source physical signal are correlated with these instants, said step for detecting comprises:
  a step for projecting the observed physical signal along a vector of form p of the reference signal, said step for projecting delivering a projected value $u_i$ for each instant of interest $(t_1, \ldots t_K)$;
  a first step for initializing a variable j at one;
  a second step for initializing a variable $u_{1:j}$ corresponding to an average of j projected values;
  a step for determining (705) the following elements: $|u_{1:j}|$, $\lambda_{1:j}^{(h)}$ and $\lambda_{1:j}^{(l)}$ with $\lambda_{1:j}^{(h)}=Q_{|\tau+w_{1:j}|}(1-\gamma_1)$, $\lambda_{1:j}^{(l)}=Q_{|\tau+w_{1:j}|}(\gamma_1)$ where $Q_{|\tau+w_{1:j}|}(\bullet)$ is the quantile function of the random variable $|\tau+w_{1:j}|$ where $w_{1:j}$ corresponds to an average of j projections of said physical disturbance signal along said vector of form p;
  a step for comparing (706) comprising comparisons between said determined elements for an instant $t_j$, and when $|u_{1:j}|>\lambda_{1:j}^{(h)}$ then an anomaly is detected, when $|u_{1:j}|\leq\lambda_{1:j}^{(l)}$ then no deviation is detected and when $\lambda_{1:j}^{(l)}<|u_{1:j}|\leq\lambda_{1:j}^{(h)}$ the variable j is incremented and the second step for initializing and the steps for determining and comparing are reiterated.

Thus, in this embodiment, such a hypothesis test uses only said first tolerance value, said first rate of tolerated false alarms and said pieces of data obtained from a treatment of the observed signal. This hypothesis test therefore does not necessitate the explicit knowledge of the model of the reference signal.

According to one particular aspect of the invention, such a method for detecting is characterized in that the number of iterations of the second step for initializing and of the steps for determining and comparing is limited by a given value M, smaller than K, and in that a final test consisting in comparing $|u_{1:M}|$ with only $\lambda_{1:M}^{(h)}$ is done, the test detecting an anomaly when $|u_{1:M}|>\lambda_{1:M}^{(h)}$.

According to one particular aspect of the invention, such a method for detecting is characterized in that said vector of form p of the reference signal is obtained by using a regression technique on the basis of a model of the reference signal.

According to one particular aspect of the invention, such a method for detecting is characterized in that said vector of form p of the reference signal is obtained by the use of a technique of estimation from the observed physical signal.

According to one particular aspect of the invention, such a method for detecting is characterized in that, when said set E corresponds to a time span, said step for detecting comprises:
- a step for obtaining a sample, sized L, of the observed signal;
- a step for obtaining a sample, sized L, of the reference signal;
- a step for determining a value corresponding to a norm of the difference between the two samples obtained;
- a step for comparing said value with a third threshold $\lambda_{\gamma_1}^* = \lambda_{\gamma_1}(\tau)$ where the function $\lambda_{\gamma_1}(\rho)$ corresponds to the unique solution, in $\eta$, of the equation $1 - R(\rho,\eta) = \gamma_1$, where the function $R(\rho, \cdot)$ corresponds to the distribution function of the square root of any unspecified random variable according to a non-centered $\chi^2$ distribution law with L degrees of freedom and defined by the parameter $\rho^2$, said step for comparing corresponding to said hypothesis test and enabling the detection of an anomaly when said value is greater than said third threshold $\lambda_{\gamma_1}^* = \lambda_{\gamma_1}(\tau)$.

According to one particular aspect of the invention, such a method for detecting is characterized in that said observed signal corresponds to a signal belonging to the group comprising: a signal called an electrocardiogram signal, a signal called a electroencephalogram signal, a signal representing a progress of arterial pressure, a signal representing a progress of a concentration of oxygen in the tissues, a signal representing a progress of intra-cranial pressure, a signal representing the progress of a respiratory flow.

According to one particular aspect of the invention, such a method for detecting is characterized in that said physical disturbance signal X(t) is Gaussian.

Another embodiment of the invention proposes a computer program product comprising program code instructions for the implementing of the above-mentioned method (in any one of its different embodiments) when said program is executed by a computer.

Another embodiment of the invention proposes a computer-readable and non-transient storage medium storing a computer program comprising a set of instructions executable by a computer to implement the above-mentioned method (in any one of its different embodiments).

Another embodiment of the invention proposes a device for detecting the presence of an anomaly Δ(t) included in an observed physical signal Y(t), said observed signal comprising an addition of a physical disturbance signal X(t), and a reference signal f(t), and said anomaly being relative to a modification of the behavior of the reference signal f(t) relative to a first tolerance value $(\tau,\tau_0)$. Such a device is characterized in that it comprises:
- means for determining a temporal set E comprising at least one instant of interest $(t_k; \{t_1, \ldots, t_K\})$;
- means for detecting the presence of said anomaly within said observed physical signal, on said set by means of a performance of a hypothesis test, using said first tolerance value $(\tau,\tau_0)$, a first rate of tolerated false alarms $\gamma_1$, and data (p,Y) obtained from a treatment of the observed signal.

In another embodiment of the invention, such a detection device is characterized in that the detection means comprise:
- means for projecting the observed physical signal along a vector of form p of the reference signal, said means for projecting delivering a projected value u for said at least one instant of interest $(t_k)$; and
- means for comparing an absolute value of said projected value u and a second threshold $\lambda_{\gamma_1}^* = Q_{|\tau+w|}(1-\gamma_1)$ where $\gamma_1$ is said rate of tolerated false alarms, $\tau$ is said first value of tolerance, Q is a quantile function of a random variable $|\tau+w|$ where w is a projection of said physical disturbance signal, along said vector of form p, said means for comparing performing said hypothesis test and enabling the detection of an anomaly when the absolute value of said projected value u is above said second threshold $\lambda_{\gamma_1}^*$

5. LIST OF FIGURES

Figure 3:
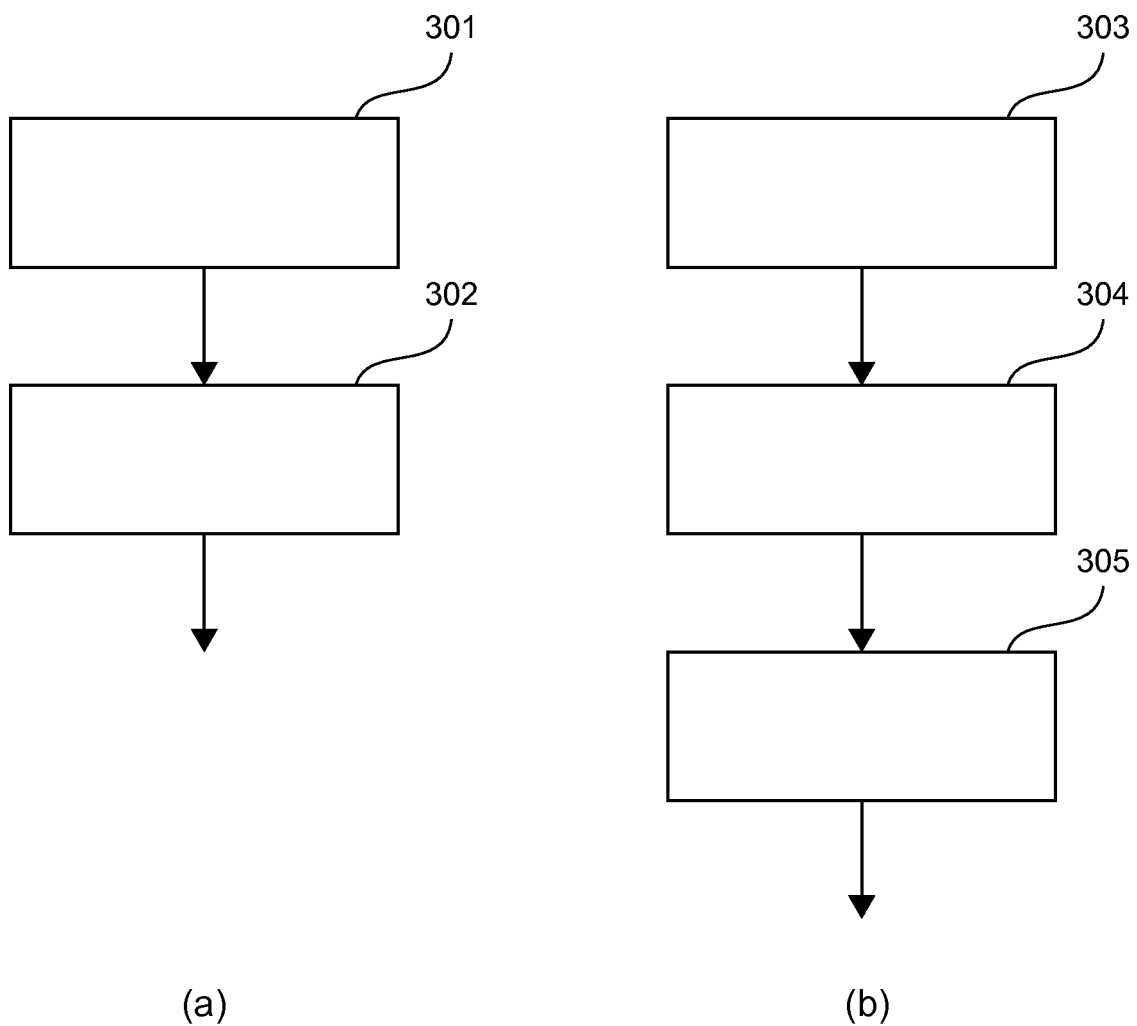
Figure 4:
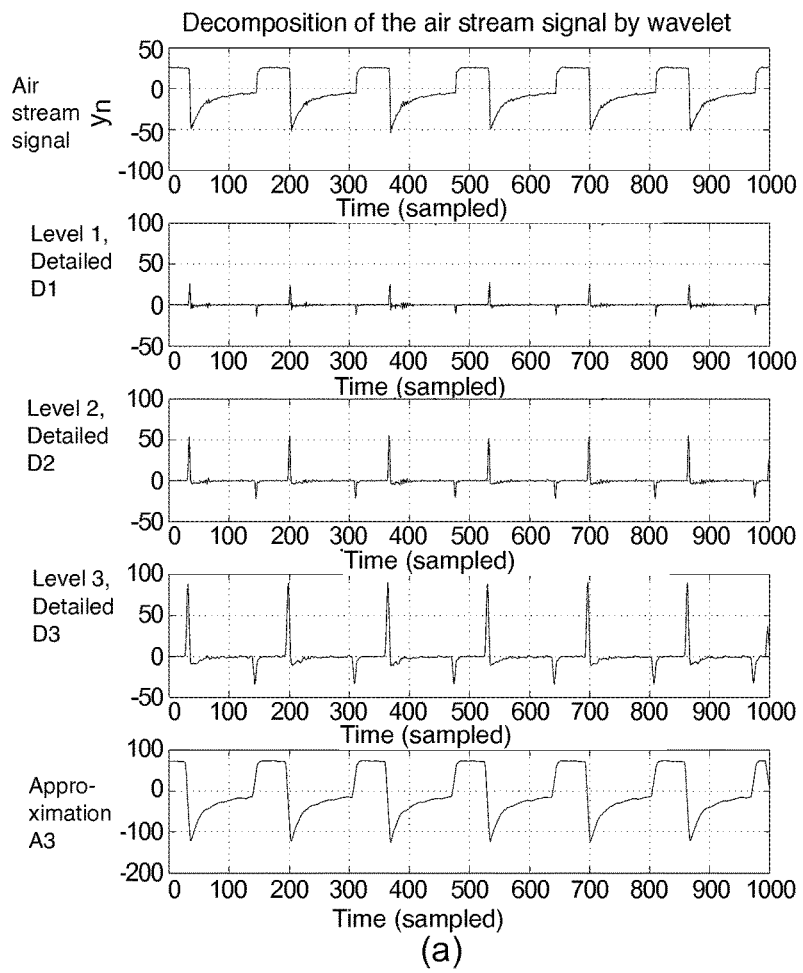
Figure 4:
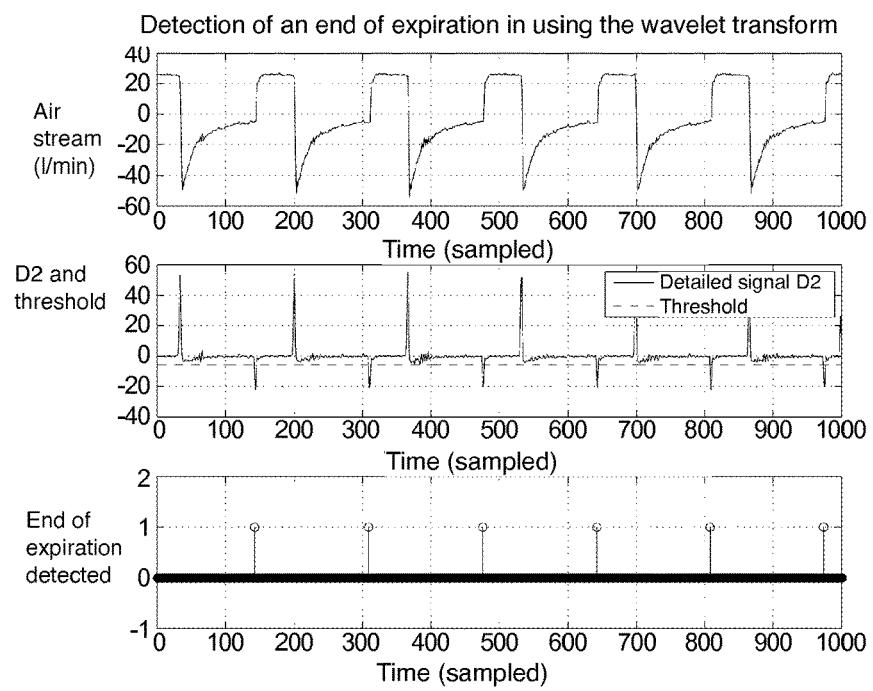
Figure 5:
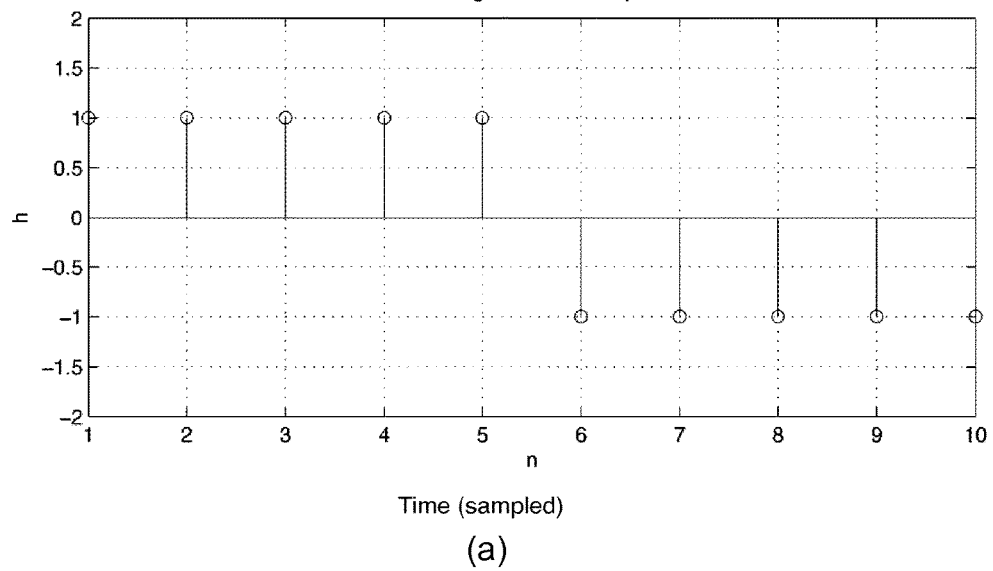
Figure 5:
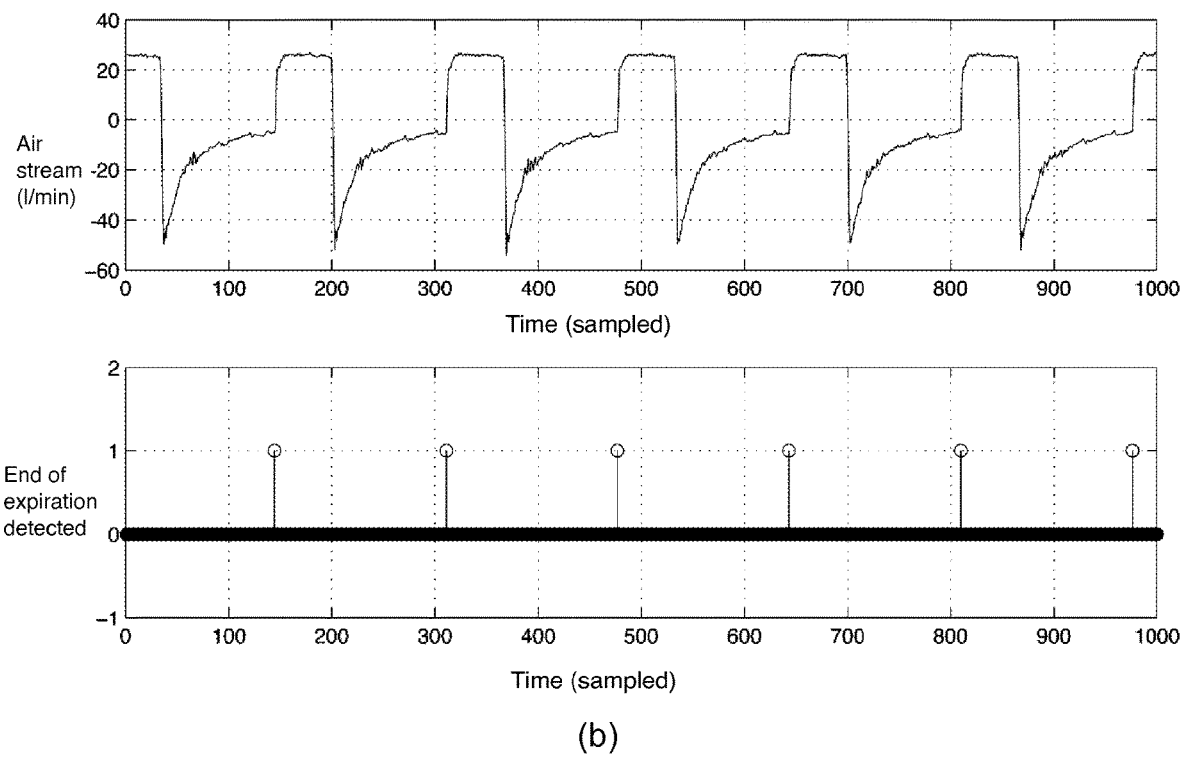
Figure 6:
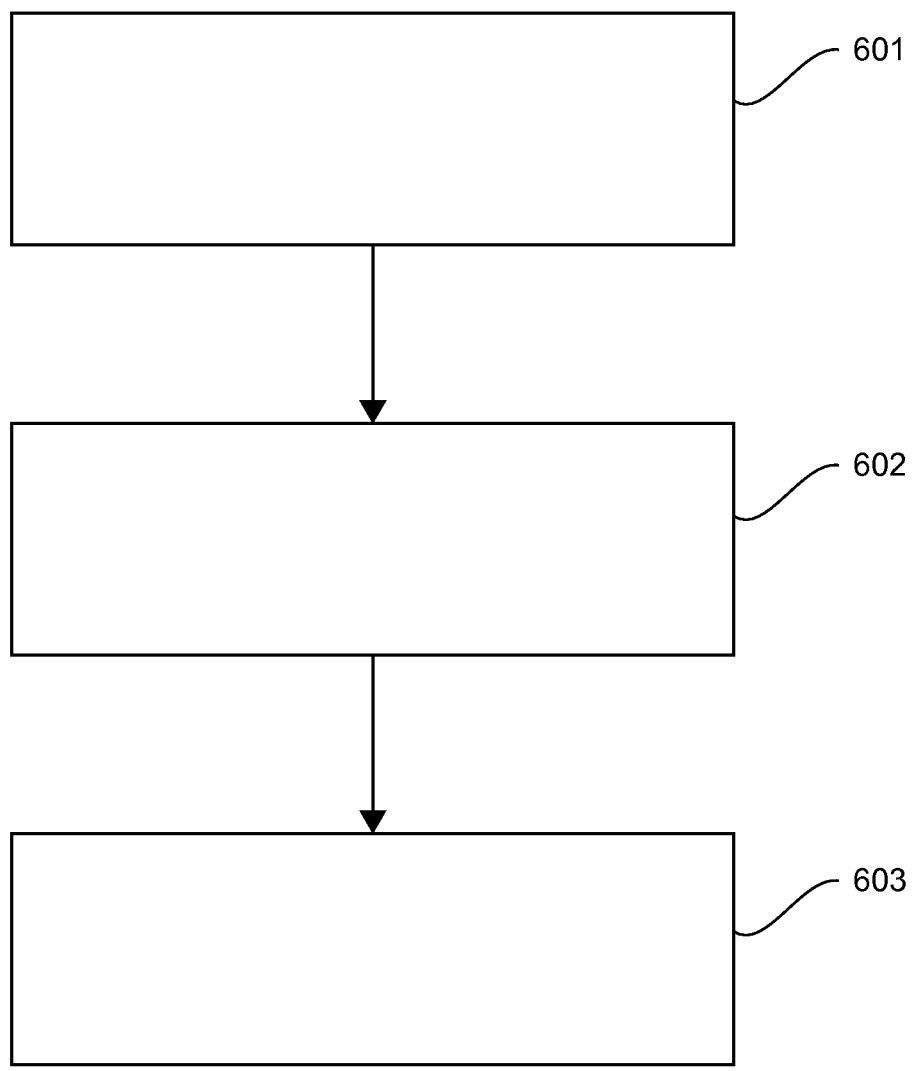
Figure 7:
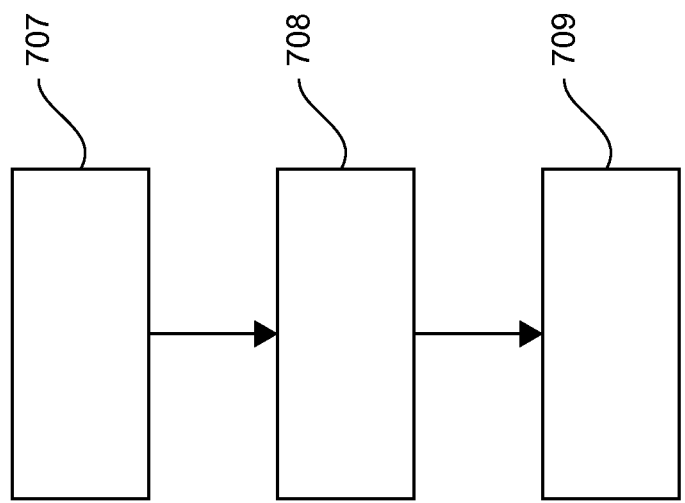
Figure 7:
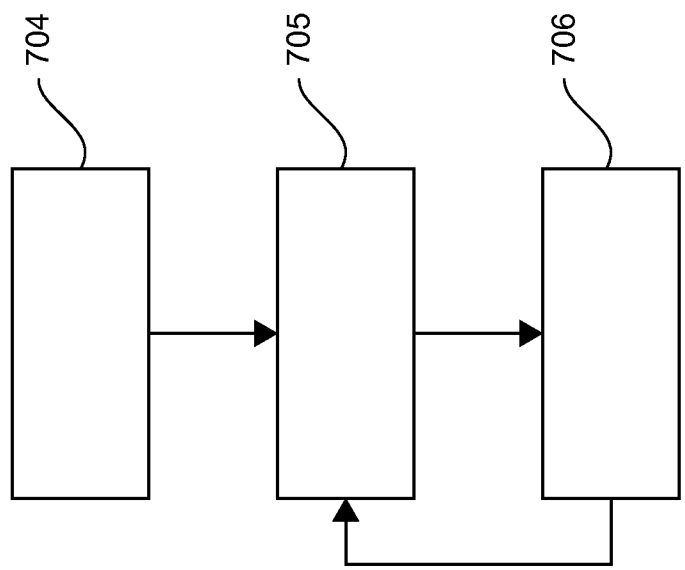
Figure 7:
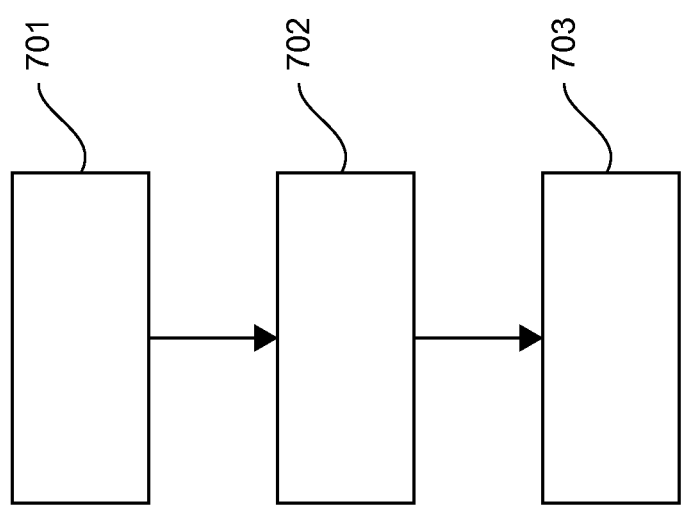

Other features and advantages of the invention shall appear from the reading of the following description, given by way of an indicative and non-exhaustive example and from the appended drawings, of which:

FIG. 1 presents a simplified architecture of a device for detecting Auto-Peep according to one particular embodiment of the invention;

FIG. 2(*a*) presents the characteristic phases of a signal during a respiration comprising an inspiration and an expiration;

FIG. 2(*b*) presents a signal representing the progress of the respiratory flow of a patient as a function of time, said signal comprising a plurality of respiration cycles, as well as instants of interest for the detection of Auto-Peep;

FIG. 3(*a*) presents the steps implemented by a module for detecting at least one instant of interest $t_k$ according to one particular embodiment of the invention;

FIG. 3(*b*) presents steps implemented by a module for detecting at least one instant of interest $t_k$ according to another particular embodiment of the invention;

FIGS. 4(*a*) and (*b*) present curves derived from the processing described with reference to FIG. 3(*a*);

FIGS. 5(*a*) and (*b*) present curves derived from the processing described with reference to FIG. 3(*b*);

FIG. 6 presents the steps implemented by a module for estimating parameters according to one particular embodiment of the invention;

FIGS. 7(*a*), (*b*) and (*c*) present the organization, in the form of flowcharts, of the steps implemented by a module for detecting according to different embodiments of the invention.

6. DETAILED DESCRIPTION

In all the figures of the present invention, the identical elements and steps are designated by a same numerical reference.

According to one embodiment, the invention is implemented by means of software and/or hardware components. From this perspective, the term "module" can correspond in this document equally well to a software component, a hardware component or a set of hardware and software components.

A software component corresponds to one or more computer programs or one or more sub-programs of a program or more generally to any element of a program or of a piece of software capable of implementing a function or a set of functions according to what is described here below for the concerned module. Such a software component is executed by a data processor of a physical entity (terminal, server, gateway, etc) and is capable of accessing the hardware resources of this physical entity (memories, recording media, communications buses, input/output electronic boards, user interfaces, etc).

In the same way, a hardware component corresponds to any element of a hardware unit capable of implementing a function or a set of functions according what is described here below for the module concerned. It may be a programmable hardware component or a component with integrated processor for executing software, for example, an integrated circuit, a smartcard, a memory card, an electronic board for executing firmware, etc.

FIG. 1 presents a simplified architecture of a device for detecting Auto-Peep according to one particular embodiment of the invention.

Such a device 100 for detecting Auto-Peep comprises:
- a module 101 for acquiring data obtained by discretization, on the basis of a sampling period $T_s$, of an observed signal $Y(t)=\theta(t)+X(t)$ where the signal $X(t)$ is a noise coming from errors caused by measurement apparatuses or external parasitic events, and where the signal $\theta(t)$ is a signal of interest. More specifically, it must be noted that the signal of interest $\theta(t)=f(t)+\Delta(t)$ where $f(t)$ is a reference signal (i.e. the signal without anomalies, as can be observed in a healthy patient) and where $\Delta(t)$ corresponds to the signal representing anomalies (i.e. $\Delta(t)$ can be interpreted as being a random process which represents the manifestation of the anomalies that occur in a patient). Such a module 101 thus enables the performance of the formatting of the data thus acquired (and more specifically the selection of a sub-part of the data received) as a function of a temporal unit E (especially such a set can comprise one or more precise instants of interest or such a set E can be a temporal range of interest, i.e. a time span of interest) given to said module 101 by a module 102 described here below;
- a module 102 for determining a temporal set E. In this embodiment, the module 102 determines at least one precise instant of interest $t_k$ on the basis of data obtained previously, or same data acquired by the module 101 (thus, a set is obtained corresponding either to $E=\{t_k\}$ or to $E=\{t_1, \ldots, t_K\}$ where $t_1, t_2, \ldots, t_K$ are particular instants that are not necessarily consecutive). In one particular embodiment, the module 102 gives a temporal range of interest $E=[t_0;t_0+T]$ to the module 101, where $t_0$ is an instant selected by the module 102, and T is the temporal length of the temporal range of interest (thus, such a temporal range corresponds to a set of consecutive instants) in which at least one instant of interest $t_k$ is included. The module 102 carries out a particular processing in order to detect at least one instant of interest (i.e. one or more instants) as a function of characteristics inherent to the signal of interest (for example such a characteristic can be linked to the presence of a sudden change such as sharp variation of the signal of interest when this signal shows no anomalies (i.e. the reference signal)). Thus, an instant of interest belonging to a set $E=\{t_k\}$ or $E=\{t_1, \ldots, t_K\}$ can be the instant starting from which such a phenomenon of variation occurs. The temporal range of interest E can correspond to the temporal range starting at the instant from which such a phenomenon of variation occurs and having a given length T (i.e. for example $t_0=t_k$). In one particular embodiment of the invention, the reference signal $f(t)$ presents patterns which are repeated in time (in this embodiment, the module 102 does not need detailed knowledge of the behavior of the reference signal $f(t)$ in detail (i.e. the module 102 does not possess any module of the reference signal $f(t)$)). In another embodiment, the module 102 possesses a model of the reference signal $f(t)$;
- a module 103 for estimating which, on the basis of the same input data as the module 101 (namely the sampled signal as well as the temporal set E coming from the module 102 for determining), enables the estimation of different parameters such as the form of the curve of the signal of interest on a temporal range of interest (for example the form of the curve of the signal of interest relative to the patterns that are repeated as mentioned here above), a standard mean deviation or the value at a precise instant of a temporal range;
- a module 104 for detecting an anomaly in the signal of interest $\theta(t)$ (for example an anomaly such as an Auto-Peep, i.e. when $\Delta(t)\gg 0$). In order to make such a detection of the formatted data coming from the module 101, the module 104 requires the estimations of different parameters coming from the module 103 as well as parameters of configuration (namely a rate of tolerated false alarms $\gamma_1$ and a value of tolerance $\tau$, the utility of which will be described in detail further below in the present application). Thus, the module 104 implements a technique for detecting an anomaly within a signal of interest $\theta(t)$ relative to a reference signal $f(t)$ in one or more precise critical instants $t_k$, or on a temporal range, this being done on the basis of data coming from an observed signal $Y(t)$.

It must be noted that, in one alternative embodiment, the functions of the modules referenced 101, 102, 103 and 104 can also be implemented in hardware form in a programmable component of an FPGA (Field Programmable Gate Array) or ASIC (Application-Specific Integrated Circuit) type.

FIG. 2(a) presents the characteristic phases of a signal during a respiration comprising an inspiration and expiration.

Thus, during a respiration, the signal corresponding to the progress of the air flow inspired and expired by the patient can be segmented into three distinct temporal ranges as a function of the behavior of such a signal. Such a segmentation corresponds to the three stages of a respiration, namely, an inspiration which is done during a first temporal range, then a pause during a second temporal range and an expiration during a third temporal range. Thus, with reference to the description of the module 102, it must be noted that a temporal range of interest $E=[t_0;t_0+T]$ can be one of these ranges.

FIG. 2(b) presents a signal representing the progress of the respiratory flow of a patient as a function of time, said signal comprising a plurality of respiration cycles.

FIG. 3(a) presents steps implemented by a module for detecting at least one instant of interest $t_k$ according to one particular embodiment of the invention.

The module 102, in one embodiment, implements a step for decomposition of the observed signal received through the execution of a step 301 for applying a wavelet transform to the observed signal $(Y(t))$ and then the execution a step 302 for detecting a variation in the changing of the coefficients obtained and of the corresponding instant or instants, in detecting especially the crossing of a threshold resulting from the implementation of a hypothesis test. Thus, the module 102 can detect one or more instants for which the behavior of the reference function or of the signal of interest has a particular characteristic (high variation etc) and therefore enables the definition of a temporal range of interest comprising for example this instant or these instants of interest.

More specifically, on a given time period, which is generally fairly large we have $[T_1;T_2]$ where $T_1$ and $T_2$ represent times in which an observed signal is discretized with a sampling period $T_s$. Thus, in one embodiment, there is available a set of points $y_n = Y(nT_s) = \theta(nT_s) + X(nT_s) = \delta_n + x_n$ with n as an integer. For example, it is possible to obtain a sample of points of a predetermined size L. It must be noted that the discrete wavelet transform applied during the step 301 enables the transformation of L given elements defined in time into L coefficients.

Thus, by choosing an orthonormal wavelet base $g_i$, and because the decomposition into wavelets is additive, the discrete wavelet transform (implemented by the module 102) on the sample sized L of the signal $Y=[y_1, \ldots, y_L]$ makes it possible to obtain L coefficients (and makes it possible to define a vector $d=[d_1, \ldots, d_L]$) each of which verify the following equation: $d_i = \alpha_i + \beta_i$, for $i \in [[1;L]]$ where $\alpha_i$ corresponds to a wavelet coefficient of interest and $\beta_i$ corresponds to a Gaussian noise.

Thus, the orthogonal matrix W associated with the discrete wavelet transform enables the following equalities to be verified: $d=WY$, $\alpha=W\delta$ and $\beta=WX$ where $\alpha=[\alpha_1, \ldots, \alpha_L]$, $\beta=[\beta_1, \ldots, \beta_L]$, $X=[x_1, \ldots, x_L]$, $Y=[y_1, \ldots, y_L]$, $\delta=[\delta_1, \ldots, \delta_L]$ and the matrix W has the dimension L×L. Depending on the hypotheses on the processing of edge problems, such a matrix can be orthogonal or "almost orthogonal". In considering that the noise X(t) for which a sample $X=[x_1, \ldots, x_L]$ is possessed can be likened to a Gaussian noise (even through the noise X(t) does not exactly possess the same properties as a Gaussian noise) and since the base on which the projection is made is orthonormal, the noise X and the noise β have the same probabilistic properties. Indeed, since $\beta=WX$, β inherits the Gaussian nature of X, and $Cov(\beta,\beta) = E\beta^T\beta = EX^TW^TW\ X = cov(X,X) = \sigma_X^2 I$ where $\sigma_X$ is the mean standard deviation of the noise X.

At the exit from the step 301, a vector $d=[d_1, \ldots, d_L]$ is therefore obtained comprising L coefficients.

It must be noted that, when the sample is great (i.e. L is great), the absolute value of the noise, i.e. the absolute value of any unspecified one of the Gaussian noises $\beta_i$ is bounded, with a high probability, by a threshold value: $\lambda_u(L) = \sigma_X \sqrt{2\ln L} = \sigma_\beta \sqrt{2\ln L}$ (in one particular embodiment of the invention, it is possible to choose another a threshold value that is as close for example as $\lambda_u(L) = \sigma_X \sqrt{(2\ln L - \ln(\ln L))}$ or $\lambda_u(L) = 4\sigma_X$ (for large samples (L=4000))). This threshold can also be interpreted as being the minimum value (in terms of absolute value) of the signal of interest. Consequently, the problem of detecting peaks and therefore of detecting associated instants of interest amounts to performing the following hypothesis test: $(H_0): |d_i| > |\lambda_u(L)|$ relative to the hypothesis $(H_1): |d_i| \leq |\lambda_u(L)|$.

Thus, the step 302 for detecting instants of interest (and therefore possibly a temporal range of interest) comprises the following steps:
determining a first threshold $$\lambda_{SNT} = \sigma_X \lambda_{\gamma_2}\left(\frac{\lambda_u(L)}{\sigma_X}\right)$$

where $\lambda_{\gamma_2}(\rho)$ is the unique solution in η of the following equation: $1-[\Phi(\eta-\rho)-\Phi(-\eta-\rho)]=\gamma_2$, where the function $\Phi(\bullet)$ is the function of distribution of a standard normal random variable and $\gamma_2$ is a rate of tolerated or accepted false alarms. This rate is generally chosen to be very small (for example $\gamma_2 = 10^{-4}$ or $10^{-5}$ or $10^{-7}, \ldots$ );

comparing the value of $|d_i|$ with the value of the first threshold $\lambda_{SNT}$. When the following condition is verified: $|d_i| > \lambda_{SNT}$ at a given instant, then a significant deviation is detected at this instant. On the contrary, when the following condition is verified: $|d_i| \leq \lambda_{SNT}$ then no significant deviation is present at this given instant.

Thus, depending on the configuration of the module 102 by its user, it is possible to determine only a few precise instants grouped together in a temporal set E. It is also possible to define a temporal range of interest E comprising such a detected instant. In the event of detection of numerous successive peaks, only the first instant will be considered and the others will not be integrated with the temporal set.

In another embodiment, the module 102 carries out a preliminary treatment on the observed signal (Y(t)) in order to obtain a smoothed observed signal $\overline{Y(t)}$. The steps 301 and 302 are applied to a smoothed observed signal of this kind $\overline{Y(t)}$.

FIGS. 4(a) and (b) present curves derived from the treatment described with reference to FIG. 3(a).

FIG. 3(b) presents steps implemented by a module for detecting at least one instant of interest $t_k$ according to another particular embodiment of the invention.

The module 102, according to this embodiment implements a step of filtration applied to the received observed signal. Thus, a step of this kind enables the detection of one or more instants for which the behavior of the reference function or of the signal of interest has a particular characteristic (high variation, etc). Thus, a temporal range of interest can be defined through the use of a filtering step of this kind.

More specifically, and in relation with a processing of a signal as presented in FIG. 2(b), the instants of interest corresponding to the instants pertaining to an end of expiration are detected automatically by the device 100 via the module 102 implementing such a filtering step.

In one particular embodiment of the invention, such a filtering step comprises:
a step 303 for smoothing the obtained signal $Y(t)=\theta(t)+X(t)$. Thus, a smoothed observed signal $\overline{Y(t)}$ is detected;
a step for determining the sign 304 (positive or negative) of the smoothed observed signal $\overline{Y(t)}$ (should the signal correspond to a flow or air stream, the term "positive" sign is used when the air stream occurs in a first direction and the "negative" sign is used when the air stream occurs in the direction opposite to the first direction), depending on a value of tolerance Δ enabling the correction of the value of the sign obtained (i.e. if at a given instant t, the smoothed observed signal can be considered at first view to be a "positive" sign, but if the value of the smoothed observed signal at this instant is below a tolerance value Δ, then the observed signal will be considered to be "negative"). More specifically, a step of this kind consists in determining the progress of the function $\text{sign}(\overline{Y(t)}-\Delta)$ where the function $\text{sign}(\bullet)$ is the function determining a sign (positive or negative expressed respectively by the values +1 or −1). It must be noted that the tolerance value Δ can be defined preliminarily by a clinician or estimated from the representation of the function of distribution of the air stream signal;

a step 305 for determining instants of interest via the application of a filter F' to the function sign($\overline{Y(t)}-\Delta$) determined at the previous step. The filter F' corresponds for example to the filter defined by F'= [−1, ..., −1, +1, ..., +1] as shown in FIG. 5(*a*). Such a filter makes it possible to highlight the correlation of a plurality of samples. Thus, FIG. 5(*b*) and more specifically the graph at the bottom of FIG. 5(*b*) presents the result of the determining of F'*sign($\overline{Y(t)}-\Delta$) where the peaks obtained 501, 502, 503, 504, 505 and 506 correspond to the instants to be considered.

In another embodiment, when the reference signal $f(t)$ is periodic, it is possible to obtain a temporal range of interest by carrying out a temporal segmentation relative to the reference signal $f(t)$ by using techniques based on the Markov chains (for example the SSMM (Segmental Semi Markov Model) technique or the use of hidden Markov chains (HMM or Hidden Markov Model)) which are implemented in the module 102.

FIG. 6 presents steps implemented by a module for estimating parameters according to one particular embodiment of the invention.

The module 103, using data relative to the observed signal as well as a temporal set coming from the module 102, executes several steps for estimating parameters that must then be transmitted to the decision module 104.

The module 103 makes it possible, in one particular embodiment of the invention, to carry out:

an estimation 601 of a vector p representing the form of the reference signal $f(t)$ on a given time span linked to the temporal set E;

an estimation 602 of the standard deviation $\sigma_X$ of the noise X(t);

an estimation 603 of a reference $\alpha_{PEP}$ enabling the definition, from a given tolerance value $\tau_0$, of a corrected tolerance value $\tau_0 + \Delta_{PEP}$.

In a first embodiment, the step 601 for estimating the vector p representing the form of the reference signal $f(t)$ on a given time span comprises:

a step for obtaining the model of the reference signal $f(t)$ on a given time span comprising unknown parameters (for example on the time span corresponding to the end of the phase of expiration of air by a patient, such a reference signal is modeled by the function $f(x)=a-be^{-ct}$ where b>0 and c>0. The unknown parameters are the parameters a, b and c);

a step for applying a (non-linear) regression technique to the data observed on the time span considered. Thus, from a set of observation points ($t_i$, $y_i$), the value of the indeterminate parameters is determined (in this case, with respect to the function $f(x)=a-be^{-ct}$ the parameters (a,b,c) are determined, these parameters being the solution to the following optimization problem $$\underset{a,b,c}{\text{argmin}} \sum_{i=1}^{L} w_i (y_i - (a - be^{-ct_i}))^2,$$

where the significant values $w_i$ are chosen so that the influence of certain points is reduced).

a step for determining the vector p from the result of the previous step.

In a second embodiment, when the reference signal $f(t)$ has repetitive patterns in time, the step of estimation 601 of the vector p representing the form of the reference signal $f(t)$ on a given time span comprises a step for determining an estimation of such a vector $\hat{p}$ from a sample of the data on a time span on which no anomaly is present. For example, from a sample of 2L+1 elements (for a single respiration cycle), we have the vector $\hat{p}=u_1=[\hat{p}_{-L}, \ldots, \hat{p}_0, \ldots, \hat{p}_L]^T$ which corresponds to $$\left[ \frac{\hat{\theta}(t_k - LT_s)}{\hat{\theta}(t_k)}, \ldots, 1, \ldots, \frac{\hat{\theta}(t_k + LT_s)}{\hat{\theta}(t_k)} \right]^T$$

and $\hat{\theta}(t_k \pm kT_s) = \hat{f}(t_k \pm kT))$. To obtain a more precise estimation, this step for determining is performed for K respiration cycles (without anomalies) and the estimation $\hat{p}$ corresponds to the average of the estimations obtained.

Thus, we have $$\hat{p} = \frac{1}{K} \sum_{i=1}^{K} u_i$$

In a third embodiment, the estimation 601 of the vector p can be made dynamically.

More specifically, in one embodiment of the invention, the vector is modified in taking account of a parameter $\mu \in [0;1]$ to limit the importance of the "former" estimation. Thus, we obtain $$\hat{p} = \frac{1-\mu}{1-\mu^K} \sum_{i=1}^{K} \mu^{K-i} u_i.$$

The estimation 602 of the standard deviation $\sigma_X$ of the noise X(t) can be obtained according to any one of the two steps described here below.

The first step consists in carrying out an estimation through the application of a regression technique in considering the residues obtained to be noise.

More specifically, for a single respiration cycle, from a sample of 2L+1 elements, the sample being centered, we obtain a value $$\hat{\sigma}_X = \sigma_1 = \frac{1}{2L} \sqrt{\sum_{i=0}^{2L} \left( f(t_k - (L-i)T_s) - \hat{\theta}(t_k - (L-i)T_s) \right)^2}.$$

To obtain a more precise estimation in the same way as for the estimation of the vector of form, it is appropriate to take the average of the values of the deviation obtained for K cycles of respiration (without anomalies). Thus, $$\hat{\sigma}_X = \frac{1}{K} \sum_{i=1}^{K} \sigma_i$$

In a third embodiment, the estimation 602 of the standard deviation $\sigma_X$ of the noise X(t) can be done dynamically.

More specifically, in one embodiment of the invention, the vector is modified in taking account of a parameter $\mu \in [0;1]$ making it possible to limit the importance of the "older" estimation. Thus, we obtain $$\hat{\sigma}_X = \frac{1-\mu}{1-\mu^K} \sum_{i=1}^{K} \mu^{K-i} \sigma_i.$$

The second step is a step for carrying out an estimation from the wavelet coefficients in using either a MAD (Median Absolute Deviation) type estimator or a DATE (d-dimensional adaptive trimming estimator) type estimator, when the noise X(t) is a Gaussian white noise or can be considered as capable of being likened to a Gaussian white noise. These two estimators (MAD or DATE) which use wavelet coefficients do not make it necessary to obtain the model of the function $f$ unlike in the case of the previous technique.

The step of estimation 603 of a reference $\Delta_{PEP}$ enables the definition, from a given value of tolerance $\tau_0$, of a corrected tolerance value $\tau = \tau_0 + \Delta_{PEP}$ which will be used by the module 104.

More specifically, the reference $\Delta_{PEP}$ can be obtained by observing, at a given point of interest $t_k$, the values of the signal of interest on several respiration cycles without anomalies, and by choosing $\Delta_{PEP}$ as being the mean value of these elements. Furthermore, this corrected tolerance value also had to be validated by the clinician. It is the reflection of a certain degree of limitation of the flow following the settings on the ventilator (setting of an positive expiratory pressure—extrinsic PEP).

FIGS. 7(a), 7(b) and 7(c) are flowcharts presenting the arrangement of the steps implemented by a detection module according to different embodiments of the invention.

FIG. 7(a) gives a view, in the form of a flowchart, of the arrangement of the steps implemented by a detection module according to one embodiment of the invention, to detect an anomaly in the signal of interest at a precise instant $t_k$.

The problem relating to the detection of a deviation between the signal of interest $\theta(t)$ and the reference signal $f(t)$ at a chosen critical instant $t_k$, said deviation being considered as such as a function of a tolerance value $\tau$, can be formulated as the resolution of a test enabling a choice to be made between two hypotheses, $H_0$ and $H_1$, of which one and only one is true, in the light of the formatted observed signal Y(t) obtained through the module 101. The tolerance value $\tau$ is therefore a value for which it is considered that a deviation is or is not achieved. Thus, it is considered that when the difference (or deviation) in terms of absolute value between the signal of interest $\theta(t)$ and the reference signal $f(t)$ at a chosen critical instant $t_k$ is greater than the tolerance value $\tau$ then a deviation has occurred. On the contrary, it is considered that when the difference (or the divergence) in terms of absolute value between the signal of interest $\theta(t)$ and the reference signal $f(t)$ at a chosen critical instant $t_k$ is below or equal to the tolerance value $\tau$, then the deviation (or anomaly) does not occur. Thus, the tolerance value $\tau$ makes it possible not to consider small, marginal variations of no importance in the signal of interest $\theta(t)$ compared with the reference signal $f(t)$ at a chosen critical instant $t_k$. The choice of the tolerance value depends both on the value of the prior data as well as on the practitioner's knowledge (see description of the step 603).

Thus, it is appropriate, during a performance of such a test, to choose between the following hypotheses in the light of the formatted observed signal Y(t): the hypothesis $H_0$ is that we have $|\theta(t_k)-f(t_k)|>\tau$ and the hypothesis $H_1$ is that we have $|\theta(t_k)-f(t_k)|\leq\tau$.

In one embodiment of the invention, the chosen critical instant $t_k$ being known (for example through the use of the module 102), the module 101 can set up a formatting of 2L+1 samples of the observed signal in the neighborhood of the chosen critical instant $t_k$ and give such a data sample to the module 104. In one embodiment, the samples are not distributed uniformly around the chosen critical instant $t_k$. In a preferred embodiment, it is chosen to center the 2L+1 samples on either side of the chosen critical instant $t_k$. Thus, assuming that a sampling period $T_s$ is chosen, the module 104, in one preferred embodiment of the module 101, obtains the 2L+1 samples of the observed signal Y(t), put in the shape of a column vector $Y=[Y(t_k-LT_s), \ldots, Y(t_k-T_s), Y(t_k), Y(t_k+T_s), \ldots, Y(t_k+LT_s)]^T$. By the definition of the observed signal, it becomes the following vector equation $Y=\Theta+\Omega$ where $\Theta=[\theta(t_k-LT_s), \ldots, \theta(t_k), \ldots, \theta(t_k+LT_s)]^T$ and $\Omega=[X(t_k-LT_s), \ldots, X(t_k), \ldots, X(t_k+LT_s)]^T$.

When it can be established that $\Theta=[\theta(t_k-LT_s), \ldots, \theta(t_k), \ldots, \theta(t_k+LT_s)]^T = p \cdot \theta(t_k)$ with $$p = [p_{-L}, \ldots, p_0, \ldots, p_L]^T = \left[\frac{\theta(t_k-LT_s)}{\theta(t_k)}, \ldots, 1, \ldots, \frac{\theta(t_k+LT_s)}{\theta(t_k)}\right]^T$$

and where the vector p is known (because it is obtained through the estimation made by the module 103) a step of projection is carried out so that we have:

$$\frac{p^T Y}{\|p\|_2^2} = \frac{p^T(\Theta+X)}{\|p\|_2^2} = \frac{p^T(p\theta(t_k)+X)}{\|p\|_2^2} = \theta(t_c) + \frac{p^T X}{\|p\|_2^2}$$

where the function $\|\cdot\|_2$ is the standard Euclidian norm.

Taking $$u = \frac{p^T Y}{\|p\|_2^2} \text{ and } w = \frac{p^T X}{\|p\|_2^2},$$

the equation is simplified as follows: $u=\theta(t_k)+w$. The step 701 consists in determining the value of u in using especially the estimation of the vector p given by the module 103.

Thus, through the use of the vector p (to make the projection) or more precisely its estimation, the initially multidimensional problem becomes a one-dimensional problem.

In observing that the problem of the hypothesis test remains the same as above, namely testing the hypothesis $H_0$: $|\theta(t_k)-f(t_k)|>\tau$ against the hypothesis $H_1$: $|\theta(t_k)-f(t_k)|\leq\tau$, and using "projected" data (i.e. u) and in observing that the variance of the noise $$w = \frac{p^T X}{\|p\|_2^2}$$

is smaller than that of the noise in $t_k$, the test consists then in making a comparison of the value of |u| with a discrimination threshold $\lambda_{\gamma_1}^*$ (which is a function of the rate of false alarms $\gamma_1$ tolerated or accepted by the practitioner and a tolerance value τ) which is obtained in a step 702 described here below. Thus, when the following condition is verified: $|u|>\lambda_{\gamma_1}^*$ then a significant deviation is detected at the instant $t_k$ within the signal of interest in complying with the rate of false alarms. On the contrary, when the following condition is verified: $|u|\leq\lambda_{\gamma_1}^*$ then no significant deviation is present at the instant $t_k$ within the signal of interest in complying with the rate of false alarms. Such a comparison is obtained during the step 703.

The step 702 for determining the discrimination threshold $\lambda_{\gamma_1}^*$ consists in evaluating the quantile function Q of the random variable $|\tau+w|$ in the value $(1-\gamma_1)$. It may be recalled that the quantile function Q of the random variable $|\tau+w|$ is defined as follows: $Q_{|\tau+w|}(u)=\inf(\{x/F_{|\tau+w|}(x)\leq u\})$ where the function $F_{|\tau+w|}$ corresponds to the distribution function of the random variable $|\tau+w|$, i.e. the function $F_{|\tau+w|}$ is defined as follows: $F_{|\tau+w|}(x)=P(|\tau+w|\leq x)$.

This means that obtaining the discrimination signal is done via the following computation: $\lambda_{\gamma_1}^*=Q_{|\tau+w|}(1-\gamma_1)$.

In one embodiment, when w is a centered Gaussian noise, the threshold of discrimination is determined as follows:

$$\lambda_{\gamma_1}^* = \sigma_w \lambda_{\gamma_1}\left(\frac{\tau}{\sigma_w}\right)$$

where the function $\lambda_{\gamma_1}(\rho)$ is defined as being the single solution η to the following equation: $1-[\Phi(\eta-\rho)-\Phi(-\eta-\rho)]=\gamma_1$, where the function $\Phi(\bullet)$ is a function of distribution of a standard normal random variable.

FIG. 7(*b*) presents the arrangement, in the form of a flowchart, of the steps implemented by a detection module according to one embodiment of the invention to detect an anomaly in a plurality of precise instants $t_k$.

When the module 104 wishes to detect the presence of an anomaly in a plurality of precise instants $t_k$ with $k\in[[1;K]]$ included in the temporal set E, it is necessary to ascertain whether the anomalies occurring at these instants are correlated or not. When these instants are not correlated, it is enough to iteratively apply the steps described in relation with FIG. 7(*a*).

By contrast, when they are correlated (i.e. when similar repetitive patterns are present at these instants), this information can be used to improve the method of detection in the sense that the probability of detection of false alarms is reduced and the probability of detection of anomalies is increased.

In this embodiment, the reference values at each of the instants $t_k$ are considered to be identical (namely $f=f(t_1)=f(t_2)=\ldots=f(t_K)$) (it is always possible to return to such an embodiment even when the values of the $f(t_i)$ are not identical. Indeed, it is enough to choose a value $\bar{f}$ as being the average of the value $f(t_i)$ and consider that $\bar{f}=f(t_1)=f(t_2)=\ldots=f(t_K)$). In using the same technique of projection as the one described with reference to FIG. 7(*a*), we obtain $u_k=\theta(t_k)+w_k$ for $k\in[[1;K]]\ldots$ then in taking the average we obtain $u_{1:K}=\theta_{1:K}+w_{1:K}$ with $$u_{1:K} = \frac{1}{K}\sum_{k=1}^{K} u_k,\ \theta_{1:K} = \frac{1}{K}\sum_{k=1}^{K} \theta(t_k) \text{ and } w_{1:K} = \frac{1}{K}\sum_{k=1}^{K} w_k.$$

Assuming that the reference signal does not vary excessively at the K instants $t_k$ with $k\in[[1;K]]$, the detection of an anomaly can be seen as a hypothesis test between the two following hypotheses:

$(H_0)$: $|\theta_{1:K}-f|>\tau$ $(H_1)$: $|\theta_{1:K}-f|\leq\tau$

Depending on a rate of false alarms γ tolerated or accepted by the practitioner, the decision rule is defined as follows:
If $|u_{1:K}|>\lambda_{1:K}^{(h)}$ then an anomaly is detected;
If $|u_{1:K}|\leq\lambda_{1:K}^{(l)}$ then no deviation is detected;
If $\lambda_{1:K}^{(l)}<|u_{1:K}|\leq\lambda_{1:K}^{(h)}$ then no decision can be taken in the matter. The taking of the decision is postponed to a following instant.

The upper threshold $\lambda_{1:K}^{(h)}$ is derived from the condition $1-F_{|\tau+w_{1:K}|}(\lambda_{1:K}^{(h)})=\gamma_1$.

The lower threshold $\lambda_{1:K}^{(l)}$ is derived from the condition $1-F_{|\tau+w_{1:K}|}(\lambda_{1:K}^{(l)})=1-\gamma_1$.

Where the function $F_{|\tau+w_{1:K}|}(\bullet)$ corresponds to the function of distribution of the random variable $\|\tau+w_{1:K}\|$. Thus, the two thresholds are computed as follows:

$$\lambda_{1:K}^{(h)}=Q_{|\tau+w_{1:K}|}(1-\gamma_1)$$

$$\lambda_{1:K}^{(l)}=Q_{|\tau+w_{1:K}|}(\gamma_1)$$

where $Q_{|\tau+w_{1:K}|}(\bullet)$ is the corresponding quantile function.

When the variable $w_{1:K}$ is centered and Gaussian, we obtain the explicit formulae below:

$$\lambda_{1:K}^{(h)} = \sigma_{w_{1:K}}\lambda_{\gamma_1}\left(\frac{\tau}{\sigma_{w_{1:K}}}\right)$$

$$\lambda_{1:K}^{(l)} = \sigma_{w_{1:K}}\lambda_{1-\gamma_1}\left(\frac{\tau}{\sigma_{w_{1:K}}}\right)$$

where $\lambda_{\gamma_1}(\rho)$ is the only solution in η of the equation: $1-[\Phi(\eta-\rho)-\Phi(-\eta-\rho)]=\gamma_1$
and $\lambda_{1-\gamma_1}(\rho)$ is the only solution in η of the equation: $1-[\Phi(\eta-\rho)-\Phi(-\eta-\rho)]=1-\gamma_1$, and the function $\Phi(\bullet)$ is the function of distribution of a standard normal random variable. The element $\sigma_{w_{1:K}}$ is considered to be obtained via the estimation module 103.

Thus, the method of detection of an anomaly comprises:
a step 704 for determining initialization of variables: j:=1;
a step 705 for determining the following elements: $|u_{1:j}|$, $\lambda_{1:j}^{(h)}$ et $\lambda_{1:j}^{(l)}$;
a comparison step 706 for carrying out the following operations at an instant $t_j$.
If $|u_{1:j}|>\lambda_{1:j}^{(h)}$ then an anomaly is detected;
If $|u_{1:j}|\leq\lambda_{1:j}^{(l)}$ then no deviation is detected;
If $\lambda_{1:j}^{(l)}<|u_{1:j}|\leq\lambda_{1:j}^{(h)}$ then no deviation can be taken in this case. The taking of a decision is postponed to the test made at a following instant. Thus, in this case, the variable j is incremented (i.e. j:=j+1), and the steps 705 and 706 are reiterated up to the processing of $|u_{1:K}|$ if none of the preceding comparisons has resulted in the detection of an anomaly.

So that the execution of such a decision method is not excessively lengthy, it is preferable to limit the number of iterations so that a decision is taken up to a number M, and ultimately to carry out a final test for comparing $|u_{1:M}|$ with only $\lambda_{1:M}^{(h)}$.

If $|u_{1:M}|>\lambda_{1:M}^{(h)}$ then an anomaly is detected, if $|u_{1:M}|\leq\lambda_{1:M}^{(h)}$ then no anomaly is detected.

FIG. 7(*c*) presents the arrangement, in the form of a flowchart, of the steps implemented by a detection module according to one embodiment of the invention to detect an anomaly on a time span or a temporal range $E=[t_0;t_0+T]$.

In one embodiment, the decision module 104 is considered to obtain:

a sample of L data of the observed signal Y=[$y_1, \ldots, y_L$], coming from the module 101;

a sample of L data of the reference signal F=[$f_1, \ldots, f_L$] (where $f_k = f(k \cdot T_s)$), obtained either via the estimation module 103 (if the reference signal is periodic) or, if there is a modeling of the reference signal available, it is obtained by the application of such a model. Thus, this embodiment requires the use of a sample of the reference module unlike in the other two embodiments.

The problem pertaining to the detection of a deviation between the signal of interest $\theta(t)$ and the reference signal $f(t)$ on a given time span E=[$t_0;t_0+T$] amounts to making the following hypothesis test consisting in choosing between the following two hypotheses in the light of the formatted observed signal Y(t): the hypothesis $H_0$ is that we have $\|Y-F\| > \tau$ and the hypothesis $H_1$ is that we have $\|Y-F\| \leq \tau$.

A Mahalanobis norm is chosen defined for a vector v, with the dimension L, as follows: $\|v\| = (v^T C^{-1} v)^{1/2}$ where C is the matrix of covariance of the signal noise.

In one embodiment of the invention, this matrix is deemed to be known.

In another embodiment of the invention, it is considered that this matrix is obtained via an estimation step in assuming that the noise of the signal is colored.

Depending on the rate of false alarms $\gamma$ tolerated or accepted by the practitioner, it is possible to detect an anomaly on the given time span E=[$t_0;t_0+T$] by comparing, at a step 709, the value of $\|Y-F\|$, obtained during a step 707 with a threshold $\lambda_{\gamma_1}^*$ which is determined in a step 708 which is described here below. Thus, when $\|Y-F\| > \lambda_{\gamma_1}^*$, it means that an anomaly is present on a given time span E=[$t_0;t_0+T$]. And, on the contrary, when $\|Y-F\| \leq \lambda_{\gamma_1}^*$, it means that no anomaly is present on the given time span E=[$t_0;t_0+T$].

The threshold $\lambda_{\gamma_1}^*$ determined during the step 708 is derived from the following condition: $1 - F_{\|\Delta + X\|}(\lambda_\gamma^*) \leq \gamma_1$ for any value of $\Delta$ verifying $\|\Delta\| \leq \tau$, where the function $F_{\|\Delta+X\|}$ corresponds to the function of distribution of the random variable $\|\Delta + X\|$.

Thus, the step 708 for determining the threshold $\lambda_{\gamma_1}^*$ comprises a step for determining the unique element $\eta$ of the equation $1 - R(\rho, \eta) = \gamma_1$, corresponding to $\lambda_{\gamma_1}(\rho)$, then a step for determining $\lambda_{\gamma_1}^* = \lambda_{\gamma_1}(\tau)$ and where the function $R(\rho, \cdot)$ corresponds to the distribution function of the square root of any unspecified random variable according to a law of non-centered $\chi^2$ distribution with L degrees of freedom and defined by the parameters $\rho^2$.

At least one embodiment of the present disclosure provides a technique for detecting anomalies in a signal (respiratory flow curve, etc) that is precise.

At least one embodiment of the present disclosure provides a technique of this kind that can be easily configured by a user.

At least one embodiment of the present disclosure provides a technique of this kind that works in real time.

At least one embodiment of the present disclosure provides a technique of this kind that costs little to implement.

At least one embodiment of the present disclosure provides a technique of this kind that does not require the implementing of automatic learning techniques.

At least one embodiment of the present disclosure provides a technique of this kind that does not require the use of data bases.

At least one embodiment of the present disclosure provides a technique of this kind that can be implemented without the use of intrusive methods.

At least one embodiment of the present disclosure provides a technique of this kind that does not require the use of the dispatch of another signal, such a technique being possibly qualified as a passive technique.

At least one embodiment of the present disclosure provides a technique of this kind that is simple to implement.

At least one embodiment of the present disclosure provides a technique of this kind that does not require the use of a plurality of sensors.

At least one embodiment of the present disclosure provides a technique of this kind that can be applied to numerous types of signals.

Although the present disclosure has been described with reference to one or more examples, workers skilled in the art will recognize that changes may be made in form and detail without departing from the scope of the disclosure and/or the appended claims.

The invention claimed is:

1. A method for detecting an anomaly in respiratory flow of a patient on artificial respiration comprising:
   receiving an observed physical signal by a detecting device of a respiratory flow of a patient on artificial respiration, the observed signal including respiration stages of the respiratory flow including an inspiration during a first temporal range, which is followed by a pause during second temporal range, which is followed by an expiration during a third temporal range; and
   detecting, by the detecting device, presence of an anomaly $\Delta(t)$ included in the observed physical signal Y(t), which represents progress of a patient's physiological parameters, said observed physical signal comprising an addition of a physical disturbance signal X(t), and a reference signal $f(t)$, and said anomaly being related to a modification of the reference signal $f(t)$ relative to a first predetermined tolerance value $(\tau, \tau_0)$, wherein detecting comprises the following acts performed by a data processor of the detecting device:
   determining a temporal set E comprising at least one instant of interest ($t_k$; $\{t_1, \ldots, t_K\}$), wherein the temporal set E corresponds to one of the first, second or third temporal ranges; and
   detecting the presence of said anomaly within said observed physical signal in said temporal set E by carrying out a hypothesis test using said first predetermined tolerance value $(\tau, \tau_0)$, a first rate of tolerated false alarms $(\gamma_1)$, and data (p,Y) obtained from a processing of the observed signal Y(t).

2. The method according to claim 1, wherein determining further comprises:
   obtaining coefficients by applying a wavelet transform to the observed signal during a time of observation;
   obtaining said at least one instant of interest when the absolute value of one of said coefficients is above a first threshold $\lambda_{SNT}$ by comparing the absolute values of said coefficients with the first threshold where:
   $\lambda_{SNT} = \sigma_X \lambda_{\gamma_2}(\rho)$ and where $$\rho = \left(\frac{\lambda_u(L)}{\sigma_X}\right) \text{ and } \lambda_{\gamma_2}(\rho)$$

and $\lambda_{\gamma_2}(\rho)$ is the unique solution in $\eta$ of the following equation: $1 - [\Phi(\eta - \rho) - \Phi(-\eta - \Sigma)] = \gamma_2$, where the function $\Phi(\cdot)$ is the function of distribution of a standard normal random variable, $\gamma_2$ is a second rate of tolerated false alarms, $\sigma_X$ is the deviation of the noise X(t), L is a size of the sample of said observed signal and a is approximately $\sqrt{2\ln L}$.

3. The method according to claim 2, wherein detecting further comprises:
  obtaining a projected value u for said at least one instant of interest ($t_k$) by projecting the observed physical signal along a vector of form p of the reference signal; and
  detecting said anomaly when an absolute value of said projected value u is above a second threshold $\lambda_{\gamma_1}^* = Q_{|\tau+w|}(1-\gamma_1)$ where $\gamma_1$ is said rate of tolerated false alarms, $\tau$ is said first tolerance value, Q is a quantile function of a variable $|\tau+w|$ where w is a projection of said physical disturbance signal, along said vector of form p.

4. The method according to claim 3, wherein said vector of form p of the reference signal is obtained by using a regression technique on the basis of a model of the reference signal.

5. The method according to claim 3, wherein said vector of form p of the reference signal is obtained by using a technique of estimation from the observed physical signal.

6. The method according to claim 1 wherein determining further comprises a filtering step.

7. The method according to claim 1, wherein the method further comprises smoothing the observed signal.

8. The method according to claim 1, wherein, when said set E comprises K instants of interest ($t_1, \ldots t_K$) and when the values of the observed physical signal are correlated with these instants, said detecting further comprises:
  obtaining a projected value $u_1$ for each instant of interest ($t_1, \ldots t_K$) by projecting the observed physical signal along a vector of form p of the reference signal;
  initializing a variable j at one;
  initializing a variable $u_{1:j}$ corresponding to an average of j projected values;
  determining the following elements: $|u_{1:j}|$, $\lambda_{1:j}^{(h)}$ and $\lambda_{1:j}^{(l)}$ with $\lambda_{1:j}^{(h)} = Q_{|\tau+w_{1:j}|}(1-\gamma_1)$, $\lambda_{1:j}^{(l)} = Q_{|\tau+w_{1:j}|}(\gamma_1)$ where $Q_{|\tau+w_{1:j}|}(\bullet)$ is the quantile function of the variable $|\tau+w_{1:j}|$ where $w_{1:j}$ corresponds to an average of j projections of said physical disturbance signal along said vector of form p;
  comparing said determined elements for an instant $t_j$, and when $|u_{1:j}| > \lambda_{1:j}^{(h)}$ then the anomaly is detected, when $|u_{1:j}| \leq \lambda_{1:j}^{(l)}$ then no deviation is detected and when $\lambda_{1:j}^{(l)} < |u_{1:j}| \leq \lambda_{1:j}^{(h)}$ then the variable j is incremented and the acts of initializing, determining and comparing are reiterated.

9. The method according to claim 8, wherein the number of iterations of the initializing the variables j and $u_{1:j}$, determining and comparing is limited by a given value M, smaller than K, and wherein a final test comprising comparing $|u_{1:M}|$ with only $\lambda_{1:M}^{(h)}$ is done, the test detecting the anomaly when $|u_{1:M}| > \lambda_{1:M}^{(h)}$.

10. The method according to claim 1, wherein when said set E corresponds to a time span (E=[$t_0;t_0+T$]) where T represents the temporal length of said time span, said detecting comprises:
  obtaining a sample, sized L, of the observed signal (Y=[$y_1, \ldots, y_L$]);
  obtaining a sample, sized L, of the reference signal, (F=[$f_1, \ldots, f_L$]);
  determining a value corresponding to a norm of the difference between the two samples obtained;
  detecting the anomaly when said value is greater than a third threshold $\lambda_{\gamma_1}^* = \lambda_{\gamma_1}(\tau)$ where the function $\lambda_{\gamma_1}(\tau)$ corresponds to the unique solution, in $\eta$, of the equation $1-R(\tau,\eta)=\gamma_1$, where the function $R(\tau,\bullet)$ corresponds to the distribution function of the square root of any unspecified random variable according to a non-centered $\ldots \chi^2$ distribution law with L degrees of freedom and defined by the parameter $\tau^2$.

11. The method according to claim 1, wherein said observed signal corresponds to a signal belonging to the group consisting of: a signal called an electrocardiogram signal, a signal called a electroencephalogram signal, a signal representing a progress of arterial pressure, a signal representing a progress of a concentration of oxygen in the tissues, a signal representing a progress of intra-cranial pressure, a signal representing the progress of a respiratory flow.

12. The method according to claim 1, wherein said physical disturbance signal X(t) is Gaussian.

13. A non-transitory storage medium comprising a computer program product stored thereon having program code instructions for implementing a method for detecting presence of an anomaly $\Delta(t)$ included in an observed physical signal Y(t) representing respiratory flow of a patient on artificial respiration and progress of a patient's physiological parameters, the observed signal including respiration stages of the respiratory flow including an inspiration during a first temporal range, which is followed by a pause during second temporal range, which is followed by an expiration during a third temporal range, wherein when said program is executed by a computer of a detecting device, said observed signal comprising an addition of a physical disturbance signal X(t), and a reference signal $f(t)$, and said anomaly being relative to a modification of the behavior of the reference signal $f(t)$ relative to a first tolerance value ($\tau,\tau_0$), said method comprising the following acts performed by the detecting device:
  receiving the observed physical signal by the device; and
  detecting, by the device, presence of the anomaly $\Delta(t)$ included in the observed physical signal Y(t), wherein detecting comprises:
  determining a temporal set E comprising at least one instant of interest ($t_k$; $\{t_1, \ldots, t_K\}$); and
  detecting the presence of said anomaly within said observed physical signal in said temporal set E by carrying out a hypothesis test using said first tolerance value ($\tau,\tau_0$), a first rate of tolerated false alarms ($\gamma_1$), and data (p,Y) obtained from a processing of the observed signal Y(t);
  wherein the temporal set E corresponds to one of the first, second or third temporal ranges.

14. A device for detecting the presence of an anomaly $\Delta(t)$ included in an observed physical signal Y(t) representing respiratory flow of a patient on artificial respiration, said observed signal comprising an addition of a physical disturbance signal X(t), and a reference signal $f(t)$, and said anomaly being related to a modification of the reference signal $f(t)$ relative to a first predetermined tolerance value ($\tau,\tau_0$), said device comprising:
  a processor; and
  a non-transitory computer-readable medium comprising instructions stored thereon, which when executed by the processor configure the device to perform acts comprising:
  receiving the observed physical signal by the device; and
  detecting, by the device, presence of the anomaly $\Delta(t)$ included in the observed physical signal Y(t), wherein detecting comprises:
  determining a temporal set E comprising at least one instant of interest ($t_k$; $\{t_1, \ldots, t_K\}$); and detecting the presence of said anomaly within said observed physical signal in said temporal set E by carrying out a hypothesis test using said first predetermined tolerance value $(\tau,\tau_0)$, a first rate of tolerated false alarms $(\gamma_1)$, and data $(p,Y)$ obtained from a processing of the observed signal $Y(t)$;

wherein the temporal set E corresponds to one of a first, second or third temporal ranges.

15. The device for detecting according to claim 14, wherein the device is further configured by the instructions to:

obtain a projected value u for said at least one instant of interest $(t_k)$ by projecting the observed physical signal along a vector of form p of the reference signal; and detect the anomaly when the absolute value of said projected value u is above a threshold $\lambda_{\gamma_1}^* = Q_{|\tau+w|}(1-\gamma_1)$ where $\gamma_1$ is said rate of tolerated false alarms, $\tau$ is said first value of tolerance, Q is a quantile function of a random variable $|\tau+w|$ where w is a projection of said physical disturbance signal, along said vector of form p.

* * * * *